United States Patent [19]

Mueller, Jr. et al.

[11] Patent Number: 4,790,315

[45] Date of Patent: Dec. 13, 1988

[54] PERFUSION DILATATION CATHETER AND METHOD OF MANUFACTURE

[75] Inventors: Richard L. Mueller, Jr., Mountain View; Andrew L. Lerohl, San Jose, both of Calif.

[73] Assignee: Advanced Cardiovascular Systems, Inc., Mountain View, Calif.

[21] Appl. No.: 903,028

[22] Filed: Sep. 2, 1986

[51] Int. Cl.⁴ .............................................. A61M 25/00
[52] U.S. Cl. ........................................ 128/344; 604/96
[58] Field of Search ................................... 604/96–103; 128/325, 344, 348.1

[56] References Cited

U.S. PATENT DOCUMENTS

| 3,734,100 | 5/1973 | Walker et al. | 604/103 X |
| 4,195,637 | 4/1980 | Gruntzig et al. | 128/344 X |
| 4,222,384 | 9/1980 | Birtwell | 604/103 |
| 4,573,470 | 3/1986 | Samson et al. | 604/96 X |
| 4,573,966 | 3/1986 | Weikl et al. | 604/101 X |
| 4,581,017 | 4/1986 | Sahota | 604/102 |
| 4,661,094 | 4/1987 | Simpson | 604/53 |

Primary Examiner—Dalton L. Truluck
Attorney, Agent, or Firm—Fulwider, Patton, Rieber, Lee & Utecht

[57] ABSTRACT

Perfusion dilatation catheter and method of manufacturing the same. The catheter has an elongated flexible shaft with an inflatable balloon mounted near the distal end of the shaft. A first lumen in the shaft communicates with the balloon for inflating and deflating the balloon. A second lumen extends between the proximal and distal ends of the shaft and is adapted to receive a guide wire. Openings formed in the side wall of the shaft on the proximal and distal sides of the balloon communicate with the second lumen to provide a path for blood to flow past the balloon when it is inflated.

11 Claims, 1 Drawing Sheet

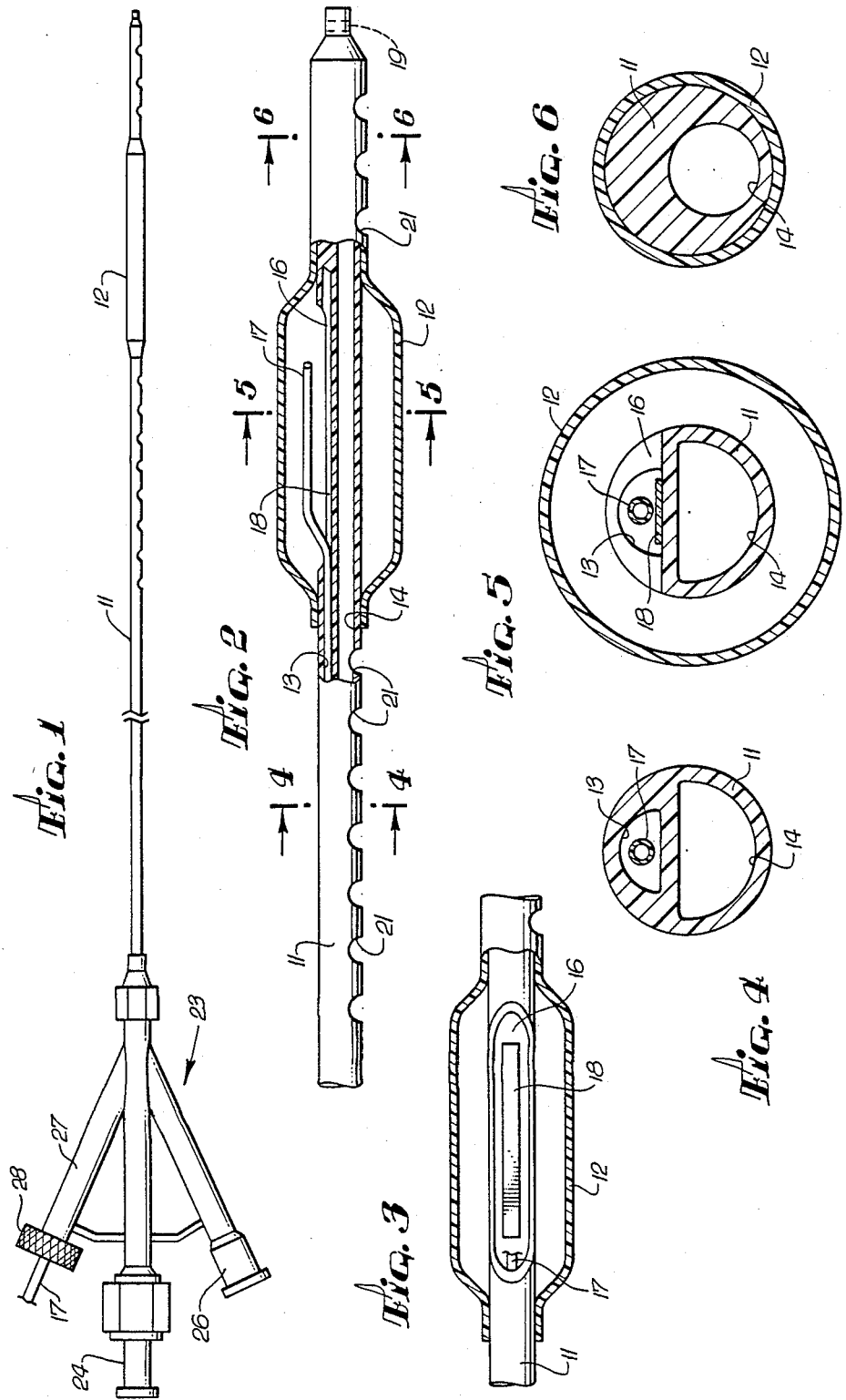

PERFUSION DILATATION CATHETER AND METHOD OF MANUFACTURE

This invention pertains generally to medical appliances, and more particularly to a perfusion dilatation catheter and method of manufacturing the same for use in coronary angioplasty.

In percutaneous transluminal coronary angioplasty, catheters are inserted into the cardiovascular system through the femoral or brachial arteries under local anesthesia. A preshaped guiding catheter is positioned in the coronary artery, and a dilatation catheter having a distensible balloon portion is advanced through this catheter into the branches of the coronary artery until the balloon portion traverses or crosses a stenotic lesion. The balloon portion is then inflated with a fluid to compress the atherosclerosis in a direction generally perpendicular to the wall of the artery, thereby dilating the lumen of the artery.

A guide wire is often employed to facilitate placement of the dilatation catheter beyond the distal end of the guiding catheter. The guide wire is inserted through the guiding catheter, and the dilatation catheter is advanced along the guide wire to the desired position in the vascular system.

Since the inflated balloon occludes the flow of blood in the artery or other vessel being treated, the balloon can only be inflated for a limited time, typically on the order of 15–60 seconds. A longer inflation time would be desirable since it would increase the probability that the vessel would remain open after the catheter is removed. With catheters heretofore provided, however, the only way to prolong the inflation is to use repeated short inflations.

It is in general an object of the invention to provide a new and improved dilatation catheter and method of manufacturing the same.

Another object of the invention is to provide a dilatation catheter and method of the above character wherein the catheter provides blood flow around the inflated balloon and permits prolonged inflation times.

These and other objects are achieved in accordance with the invention by providing a dilatation catheter having an elongated flexible shaft in which first and second lumens are formed. An inflatable balloon is mounted on the shaft toward the distal end, and the first lumen extends between the proximal end of the shaft and the balloon, communicating with the interior of the balloon through an elongated opening in the side wall of the shaft. The second lumen extends between the proximal and distal ends of the shaft, and openings in the side wall on the proximal and distal sides of the balloon provide blood flow past the balloon through this lumen.

FIG. 1 is a side elevational view of one embodiment of a perfusion dilatation catheter according to the invention.

FIG. 2 is an enlarged, fragmentary elevational view, partly broken away, of the embodiment of FIG. 1.

FIG. 3 is a fragmentary horizontal sectional view of the embodiment of FIG. 1.

FIG. 4 is a cross-sectional view taken along line 4—4 in FIG. 2.

FIG. 5 is a cross-sectional view taken along line 5—5 in FIG. 2.

FIG. 6 is a cross-sectional view taken along line 6—6 in FIG. 2.

As illustrated in the drawings, the catheter comprises an elongated flexible shaft 11 with an inflatable balloon 12 near the distal end of the shaft. Lumens 13, 14 are formed in the shaft. The two lumens are positioned side by side, and each has a generally semicircular cross-section. Lumen 13 is of smaller diameter than lumen 14, and it extends between the proximal end of the shaft and the balloon, communicating with the interior of the balloon through an elongated opening 16. This lumen is utilized for inflating and deflating the balloon. Lumen 14 extends between the proximal and distal ends of the shaft and is adapted to receive a guide wire.

A small vent tube 17 is removably inserted into the catheter to provide communication with the interior of balloon 12. The vent tube is fabricated of a material such as plastic, stainless steel or another suitable metal, or glass, and it passes through lumen 13 and opening 16 to the interior of the balloon.

Opening 14 is formed by cutting away a portion of the side wall of shaft 11 adjacent to lumen 13 to form a channel which extends substantially the length of the balloon. The side wall is cut away to a depth of about one-third of the diameter of shaft 11. A strip 18 of radiopaque material such as gold is mounted on the bottom wall of lumen 13 through opening 16. This strip extends substantially the length of the balloon. The deflated balloon can be folded into the cut-away area provided by opening 16 to give the catheter a relatively low profile.

A fluoroscopically visible tip marker 19 is provided near the distal end of the catheter. In the embodiment illustrated, this marker comprises a band of radiopaque material which surrounds shaft 11 and is secured in place by heat sealing between the shaft and the tip of the balloon.

Lumen 13 terminates near the distal end of balloon 12, and lumen 14 has a generally circular cross-section in the distal tip portion of the shaft. The diameter of this lumen is reduced at the distal end to provide a closer fit with the guide wire.

A plurality of openings 21 are formed in the side wall of shaft 11 on the proximal and distal sides of balloon 12. These openings communicate with lumen 14, and they provide a path for blood flow past the balloon when the balloon is inserted in the vascular system and inflated. There are preferably about 3 such openings on the distal side of the balloon and 5–9 such openings on the proximal side. These openings are preferably cut in the form of notches, rather than drilled holes, and they have a generally semicircular shape when viewed from the side in a direction generally perpendicular to the axes of the openings. This shape of holes has been found to provide a better blood flow than holes drilled through the side wall in a radial direction.

In FIG. 1, the catheter is illustrated in connection with a three-arm adapter 23. This adapter has a central port 24 which communicates with lumen 14, a side port 26 which communicates with lumen 13, and a side port 27 which also communicates with lumen 13. A guide wire (not shown) and/or contrast media can be inserted through port 24, and a fluid can be introduced and discharged through port 26 to inflate and deflate the balloon. Vent tube 17 is inserted and removed through side port 27, and this port is sealed by means of a thumb screw 28 and a resilient seal (not shown).

Operation and use of the catheter are as follows. The catheter is inserted into the body of a patient and advanced along a guide wire (not shown) to position balloon 12 adjacent to the lesion to be treated. Vent tube 17 is inserted through lumen 13 and opening 16, and the distal end portion of the vent tube is positioned near the distal end of the balloon. Thumb screw 28 is tightened to compress the seal ring and form a fluid-tight seal around the proximal end portion of the vent tube. The balloon is primed or prepared for use by introducing a pressurized fluid through port 26 and displacing trapped air from the balloon through vent tube 17. When all of the air has been removed, vent tube 17 is removed, and port 27 is sealed closed. Thereafter, the balloon can be inflated and deflated as desired through port 26. While the balloon is inflated, blood can flow past the balloon through openings 21 and lumen 14. This permits the balloon to remain inflated for substantially longer than is possible with other dilatation catheters where the blood flow is cut off.

The perfusion catheter is particularly suitable for use in treating leasions which have become segmented. These lesions have a flap, and they are difficult to keep open after a standard balloon has been removed. The perfusion catheter permits the flap to be held against the vessel wall for a substantially longer period of time and at a lower balloon pressure than with a standard balloon catheter. With a standard catheter, the balloon might be inflated at a pressure of about 90-100 psi for 30-50 seconds. With the perfusion catheter, the balloon might, for example, be inflated at a pressure of 60 psi for 2-15 minutes or longer. The prolonged treatment greatly increases the chance that the vessel will remain open when the catheter is removed.

Shaft 11 and lumens 13, 14 are formed by an extrusion process. Opening 16 is cut in the side wall of the shaft, and radiopaque marker 17 is applied to the bottom wall of lumen 13 beneath the opening. Balloon 12 and radiopaque tip marker are mounted on the shaft and affixed by heat sealing the end portions of the balloon to the shaft. Openings 21 are cut in the shaft from the side with a circular cutter.

The invention has a number of important features and advantages. It permits blood to flow past the balloon when it is inflated, and this permits the balloon to remain inflated substantially longer than is possible with balloon catheters heretofore provided. The prolonged treatment increases the chances that the vessel will remain open after the catheter is removed. With the deflated balloon folded into the cut-away area, the catheter has a relatively low profile.

It is apparent that a new and improved dilatation catheter and method of manufacturing the same have been provided. While only certain presently preferred embodiments have been described in detail, as will be apparent to those familiar with the art, certain changes and modifications can be made with departing from the scope of the invention as defined by the following claims.

We claim:

1. A dilatation catheter for use in angioplasty comprising an elongated flexible shaft having proximal and distal ends, an inflatable balloon concentrically mounted on the shaft near the distal end thereof, a first lumen extending within the shaft between the proximal end of the shaft and the balloon for inflating and deflating the balloon, a cylindrical segment-shaped cut-away in the flexible shaft extending along essentially the entire interior of the balloon which exposes the first lumen to the interior of the balloon and which provides an elongated surface onto which portion of the deflated balloon can be folded to thereby provide for a lower profile, a second lumen extending within the shaft between the proximal and distal ends thereof, and openings in the side wall of the shaft communicating with the second lumen on the proximal and distal sides of the balloon for carrying blood around the balloon when the balloon is inflated within a patient's artery.

2. The dilatation catheter of claim 1 including a strip of radiopaque material mounted on an relatively flat surface in the cut-away area and extending substantially the entire length of the balloon.

3. The dilution catheter of claim 1 wherein the openings in the side wall have a generally semicircular shape when viewed from the side.

4. The dilatation catheter of claim 1 wherein there are on the order of 5-9 openings communicating with the second lumen on the proximal side of the balloon and 3 openings communicating with the second lumen on the distal side of the balloon.

5. The dilatation catheter of claim 1 including a vent tube removably inserted in the first lumen and extending near the distal end of the balloon for removing trapped air from the balloon.

6. The dilatation catheter of claim 1 including a band of radiopaque material near the distal end of the shaft.

7. In a method of manufacturing a dilatation catheter for angioplasty use, the steps of: forming an elongated flexible shaft with a first lumen which extends between the proximal end and a point near the distal end of the shaft and a second lumen which extends between the proximal and distal ends of the shaft, forming a cylindrical segment-shaped cut-away in the side wall of the shaft near the distal end of the first lumen which forms an elongated surface thereon, mounting an inflatable balloon on the shaft over the cut-away, with the interior of the balloon in fluid communication with the first lumen through the cut-away and the balloon being adapted to be folded onto the elongated surface when deflated, and forming a plurality of openings in the side wall of the shaft in fluid communication with the second lumen on the proximal and distal sides of the balloon to permit blood to flow past the balloon when the balloon is inserted into the vascular system of a patient and inflated.

8. The method of claim 7 wherein the shaft is formed by extrusion.

9. The method of claim 7 wherein the elongated opening is formed by cutting away a portion of the side wall to expose the first lumen for a distance substantially equal to the length of the balloon.

10. The method of claim 7 including the step of placing a strip of radiopaque material in the exposed portion of the first lumen.

11. The method of claim 7 wherein the plurality of openings are formed in the side wall by cutting the side wall from the side with a circular cutter in a direction generally perpendicular to the axes of the openings to give the openings a generally semicircular shape from the side.

* * * * *

UNITED STATES PATENT AND TRADEMARK OFFICE
CERTIFICATE OF CORRECTION

PATENT NO. : 4,790,315

DATED : December 13, 1988

INVENTOR(S) : Richard L. Mueller, Jr. et al.

It is certified that error appears in the above-identified patent and that said Letters Patent is hereby corrected as shown below:

Column 4, line 4, delete "portion" and insert therefor --portions--.

Column 4, line 16, delete "dilution" and insert therefor --dilatation--.

Signed and Sealed this

Sixteenth Day of January, 1990

*Attest:*

JEFFREY M. SAMUELS

*Attesting Officer*     *Acting Commissioner of Patents and Trademarks*